United States Patent
Claret et al.

(10) Patent No.: US 11,224,588 B2
(45) Date of Patent: Jan. 18, 2022

(54) COMBINATION OF LIPOIC ACID AND TAURINE AS OSMOPROTECTIVE AGENT

(71) Applicant: OPHTALMIS MONACO, Monaco (MC)

(72) Inventors: Martine Claret, Saint Sulpice (CH); Claude Claret, Saint Sulpice (CH); Caroline Chatard-Baptiste, Nice (FR)

(73) Assignee: OPHTALMIS MONACO, Monaco (MC)

( * ) Notice: Subject to any disclaimer, the term of this patent is extended or adjusted under 35 U.S.C. 154(b) by 0 days.

(21) Appl. No.: 15/575,187

(22) PCT Filed: May 20, 2016

(86) PCT No.: PCT/EP2016/061358
§ 371 (c)(1),
(2) Date: Nov. 17, 2017

(87) PCT Pub. No.: WO2016/184998
PCT Pub. Date: Nov. 24, 2016

(65) Prior Publication Data
US 2018/0092878 A1    Apr. 5, 2018

(30) Foreign Application Priority Data

May 21, 2015 (FR) .................................... 1554590
Jan. 18, 2016 (FR) .................................... 1650372

(51) Int. Cl.
| | | |
|---|---|---|
| *A61K 31/385* | (2006.01) | |
| *A61K 31/185* | (2006.01) | |
| *A61K 9/00* | (2006.01) | |
| *A61K 8/46* | (2006.01) | |
| *A61K 9/06* | (2006.01) | |
| *A61K 9/14* | (2006.01) | |
| *A61K 8/49* | (2006.01) | |
| *A61P 27/02* | (2006.01) | |
| *A61P 17/00* | (2006.01) | |
| *A23L 33/10* | (2016.01) | |
| *A23L 33/175* | (2016.01) | |
| *A23L 33/12* | (2016.01) | |
| *A61Q 19/00* | (2006.01) | |
| *A23L 33/00* | (2016.01) | |

(52) U.S. Cl.
CPC ............ *A61K 31/385* (2013.01); *A23L 33/10* (2016.08); *A23L 33/12* (2016.08); *A23L 33/175* (2016.08); *A23L 33/30* (2016.08); *A61K 8/466* (2013.01); *A61K 8/4986* (2013.01); *A61K 9/0014* (2013.01); *A61K 9/0048* (2013.01); *A61K 9/06* (2013.01); *A61K 9/14* (2013.01); *A61K 31/185* (2013.01); *A61P 17/00* (2018.01); *A61P 27/02* (2018.01); *A61Q 19/007* (2013.01); *A23V 2002/00* (2013.01)

(58) Field of Classification Search
CPC .. A61K 31/105; A61K 31/385; A61K 9/0048; A61P 17/02; A61P 27/02
See application file for complete search history.

(56) References Cited

U.S. PATENT DOCUMENTS

| | | | | |
|---|---|---|---|---|
| 5,817,630 | A | * | 10/1998 | Hofmann ............. A61K 9/0048 514/20.8 |
| 6,162,393 | A | | 12/2000 | De Bruiju et al. |
| 6,277,855 | B1 | * | 8/2001 | Yerxa ..................... A61K 31/44 514/256 |
| 6,620,425 | B1 | | 9/2003 | Gardiner |
| 6,649,195 | B1 | | 11/2003 | Gorsek |
| 2001/0031744 | A1 | | 10/2001 | Kosbab |
| 2004/0265345 | A1 | | 12/2004 | Perricone |
| 2005/0192229 | A1 | | 9/2005 | Perricone |
| 2006/0127505 | A1 | | 6/2006 | Haines et al. |
| 2006/0188492 | A1 | | 8/2006 | Richardson |
| 2006/0216251 | A1 | | 9/2006 | Morariu |
| 2007/0207116 | A1 | | 9/2007 | Brown |

(Continued)

FOREIGN PATENT DOCUMENTS

| | | | |
|---|---|---|---|
| CN | 101590222 A | * | 12/2009 |
| CN | 102144780 A | | 8/2011 |
| CN | 103860625 A | | 6/2014 |

(Continued)

OTHER PUBLICATIONS

International Search Reported in Corresponding Application No. PCT/EP2016/061358 dated Jul. 19, 2016.
Kofuji et al., "Stabilization of a-lipoic acid by complex formation with chitosan" Food Chemistry—Dec. 2007, vol. 109: 167-171.
Masami Kojima et al., "Efficacy of a-Lipoic Acid Against Diabetic Cataract in Rat"Japanese Journal of Ophthalmology, Jan. 2007, vol. 51, Issue 1, pp. 10-13.

*Primary Examiner* — Theodore R. Howell
*Assistant Examiner* — George W Kosturko
(74) *Attorney, Agent, or Firm* — McBee Moore & Vanik IP, LLC

(57) ABSTRACT

The present invention relates to a combination of lipoic acid and taurine for use as an osmoprotective agent for the prevention and treatment of ailments of the skin and of the mucous membranes associated with osmotic imbalance. It also relates to a method for preventing and treating ailments of the skin and of the mucous membranes associated with osmotic imbalance, in which an appropriate amount of a combination of lipoic acid and taurine is applied to the skin or the mucous membranes of a patient who is in need thereof. The invention also relates to a pharmaceutical or cosmetic composition suitable for topical application or an oph-thalmic composition which comprises a combination oflipoic acid and taurine.

19 Claims, 2 Drawing Sheets

(56) References Cited

U.S. PATENT DOCUMENTS

2012/0258168 A1  10/2012  Montesinos

FOREIGN PATENT DOCUMENTS

| | | | |
|---|---|---|---|
| DE | 10229995 A1 | 1/2004 | |
| DE | 102009029043 A1 * | 3/2011 | ........... A61K 8/4926 |
| EP | 2311454 A2 | 4/2011 | |
| IT | 1299623 B1 * | 3/2000 | |
| JP | 2013241398 A | 12/2013 | |
| WO | WO-0072854 A1 * | 12/2000 | ............. A61K 33/24 |
| WO | 0193824 A1 | 12/2001 | |
| WO | 02098345 A1 | 12/2002 | |
| WO | 2005027950 A1 | 3/2005 | |
| WO | 2006128618 A1 | 12/2006 | |
| WO | WO-2008074579 A1 * | 6/2008 | ........... A61K 8/4986 |
| WO | 2009080220 A1 | 7/2009 | |
| WO | 2011131765 A2 | 10/2011 | |
| WO | 2012013736 A1 | 2/2012 | |
| WO | 2015150459 A1 | 8/2015 | |

* cited by examiner

COMBINATION OF LIPOIC ACID AND TAURINE AS OSMOPROTECTIVE AGENT

CROSS-REFERENCE TO RELATED APPLICATIONS

This application is a National Stage entry of International Application No. PCT/EP2016/061358, filed May 20, 2016, which claims priority to French Patent Application No. 1554590, filed May 21, 2015, and French Patent Application 1650372, filed Jan. 18, 2016.

BACKGROUND

Field of the Invention

The present invention relates to a combination of lipoic acid and taurine for use as osmoprotectant for preventing and treating diseases of the skin and of the mucous membranes associated with osmotic imbalance. It also relates to a method for preventing and treating diseases of the skin and of the mucous membranes associated with osmotic imbalance, in which an appropriate amount of a combination of lipoic acid and taurine is applied to the skin or to the mucous membranes of a patient in need thereof. The invention also relates to a pharmaceutical or cosmetic composition suitable for topical application or an ophthalmic composition which comprises a combination of lipoic acid and taurine.

Description of Related Art

Osmotic imbalance is observed in diseases of the skin and of the mucous membranes of mammals, in particular humans, generally in the form of dry skin or xerosis, which may be a sign of atopic dermatitis, ichthyosis, eczema or psoriasis; or in the form of dry eye, which may be a sign of Meibomian gland dysfunction, hyperevaporative syndrome or lacrimal insufficiency; as well as in the form of ocular edema.

The usual treatments for these diseases of the skin or of the mucous membranes include the application of moisturizing, emollient creams; corticoid-based creams or ointments; or local immunomodulators.

Taurine is a natural aminosulfonic acid produced by the pancreas of mammals by transformation of cysteine. It is known for use as a food additive in energy drinks. Use of taurine is also described in ophthalmic compositions for its properties of modulating calcium ions in cells, believed to prevent macular degeneration (US 2006/188492), or as a chelator (U.S. Pat. No. 5,817,630).

Lipoic acid, also called thioctic acid (CAS No. 1077-28-7), and derivatives thereof are known for their antioxidant properties. It is employed as a dietary supplement in tablet form (Liponsäure-Ratiopharm®, marketed in Germany by Ratiopharm) or in the form of dilute solution for injection (Neurium®, marketed in Germany by Hexal), which may be used as adjunct treatment for diabetes. Ophthalmic or cosmetic compositions which may comprise lipoic acid as antioxidant are described in the following patent applications: US 2006/188492, US 2004/265345, U.S. Pat. No. 5,817,630, WO 02098345, DE10229995, WO 01/93824, US 2005/192229, Br PI0 800 818, CN 103 860 625 and JP 2013 241398.

Its antimicrobial properties have also been described for use in contact lens cleaning solutions containing BDT (U.S. Pat. No. 6,162,393).

The antioxidant properties of lipoic acid have also been proposed to study its efficacy on cataracts in diabetic rats (Masami Kojima et al., Japanese Journal of Ophthalmology, January 2007, Volume 51, Issue 1, pp 10-13).

After having tested lipoic acid on corneal cells, the Inventors noted that the antioxidant effect observed is rather weak, weaker than the expected effect in view of what is described for dietary supplements.

They have now found that lipoic acid has significant and advantageous osmoprotective properties which allow its use in the prevention and treatment of such diseases of the skin and of the mucous membranes, notably of the eye, as a replacement for or in addition to the usual treatments, unrelated to the conditions believed to be treated by the compositions comprising lipoic acid of the state of the art. In particular, they have noted that the combination of lipoic acid and taurine increases and extends the osmoprotective effect of this combination relative to the effects observed separately for each component of the combination. Lipoic acid acts quickly after application whereas the osmoprotective effect of taurine appears and is extended when that of lipoic acid starts to decrease.

SUMMARY

The present invention relates to a combination of lipoic acid and taurine, in particular for use as osmoprotectant for preventing and treating diseases of the skin and of the mucous membranes, notably of the eye, associated with osmotic imbalance.

It also relates to a method for preventing and treating diseases of the skin and of the mucous membranes associated with osmotic imbalance, in which an appropriate amount of a combination of lipoic acid and taurine as osmoprotectant is applied to the skin or to the mucous membranes of a patient in need thereof.

It also relates to a pharmaceutical or cosmetic composition suitable for topical application or an ophthalmic composition which comprises a combination of lipoic acid and taurine.

Said combination is a combination product which comprises lipoic acid and taurine. The two components of the combination product may be comprised in the same composition or separate in two compositions employed in combination, either for extemporaneous preparation of the combination before use, or for combined use.

Advantageously, the combination comprises lipoic acid and taurine in a lipoic acid:taurine weight ratio of 0.002 to 0.2, more advantageously of about 0.004 to about 0.05, in particular of 0.005, 0.01, 0.02 or 0.1.

DETAILED DESCRIPTION OF A PREFERRED EMBODIMENT

The present invention relates to a combination of lipoic acid and taurine, in particular for use as osmoprotectant for preventing and treating diseases of the skin and of the mucous membranes, notably of the eye, associated with osmotic imbalance.

According to the invention, "lipoic acid" means 5-(1,2-dithiolan-3-yl)pentanoic acid, in racemic form or as enantiomers in any proportion, in particular the R enantiomer, pure or as a mixture where the proportion of the R enantiomer is greater than that of the S enantiomer, and the pharmaceutically acceptable salts thereof.

According to the invention, "pharmaceutically acceptable salts" advantageously include addition salts of lipoic acid with a pharmaceutically acceptable base, whether an organic base notably comprising an amino group, such as ammonia, lysine, arginine and other known compounds of the pharmacopeia, or a pharmaceutically acceptable inorganic base such as sodium hydroxide, potassium hydroxide, calcium hydroxide and other known inorganic bases of the pharmacopeia. Preferably, the pharmaceutically acceptable salt is an alkali-metal (sodium, potassium) salt, an alkaline-earth-metal (calcium, magnesium) salt or an aluminum ion, more preferably a sodium salt.

According to a preferred embodiment of the invention, the lipoic acid employed in the combination according to the invention is a salt of the R enantiomer of lipoic acid, in particular the sodium salt (CAS No. 176110-81-9) or the magnesium salt.

According to the invention, "taurine" means 2-aminoethanesulfonic acid, diastereoisomers thereof, pure or mixtures thereof in any proportion and pharmaceutically acceptable salts thereof.

It may be natural or synthetic in origin.

Taurine salts may be salts of acids or of bases. Advantageously, the taurine employed in the combination according to the invention is a mixture of diastereoisomers of 2-aminoethanesulfonic acid, in particular obtained by chemical synthesis.

Advantageously, the combination comprises lipoic acid and taurine in a lipoic acid:taurine weight ratio of 0.002 to 0.2, more advantageously of about 0.004 to about 0.05, preferably of about 0.005 to about 0.02, in particular of about 0.005, 0.01, 0.02 or 0.04.

The combination according to the invention is a combination product which comprises lipoic acid and taurine. The two components of the combination product may be comprised in the same composition or separate in two compositions employed in combination, either for extemporaneous preparation of the combination before use, or for simultaneous use.

In the case of two separate compositions for combined simultaneous use, each composition is advantageously a topical composition suitable for application to the skin or to the mucous membranes, notably to the eye.

In the case of two separate compositions for combined use for extemporaneous preparation, at least one of the compositions comprising lipoic acid or taurine is advantageously a topical composition suitable for application to the skin or to the mucous membranes, notably to the eye.

The weight ratios between the two components of the combination correspond to the proportion of each component in the extemporaneous preparation, or to the relative amount of each composition comprising lipoic acid and taurine when they are employed simultaneously.

Advantageously, the combination of lipoic acid and taurine is employed in a topical composition suitable for application to the skin or to the mucous membranes, notably to the eye.

Topical compositions are well-known to a person skilled in the art in the fields of cosmetics and pharmaceuticals.

They appear in all standard forms known to a person skilled in the art for topical application, notably in suspension or dispersion form in solvents or fats, in vesicle dispersion form or in emulsion form such as a cream or a milk, in the form of an ointment, a gel, a salve, a solid stick, an aerosol foam or a spray.

The compositions of the invention may comprise the conventional additives used for the preparation of such formulations, such as fats, organic solvents, ionic zwitterionic or nonionic surfactants, softeners, antioxidants, opacifiers, stabilizers, ionic or nonionic thickeners, silicones, antifoaming agents, moisturizing agents, vitamins, fragrances, preservatives, fillers, sequestrants, colorants, bases or acids necessary for regulation of pH, or any other ingredient commonly used for the preparation of cosmetic or pharmaceutical compositions. The compositions according to the invention are prepared according to the techniques well-known to a person skilled in the art.

According to an embodiment of the invention, the combination of lipoic acid and taurine is used in combination with other active agents, such as another osmoprotectant, an anti-inflammatory agent and/or an antioxidant.

Among the other osmoprotectants able to be employed according to the invention, mention may be made of glycerin, L-carnitine, erythritol, trehalose, ectoine, betaine, sarcosine and urea, preferably glycerin.

Among the agents with anti-inflammatory activity able to be employed with lipoic acid, mention may be made of dexamethasone, flurbiprofen, fluorometholone, salicylic acid, hydrocortisone, triamcinolone and rimexolone, preferably flurbiprofen and dexamethasone.

As other active agents, mention may also be made of derivatives or analogues of retinoic acid, in particular retinol and derivatives thereof, notably esters thereof, in particular fatty acid esters thereof such as retinyl palmitate.

Lipoic acid and the other agent(s) with anti-inflammatory activity, in particular hydrocortisone and dexamethasone, may be employed together in the same composition or in separate compositions.

Among the antioxidants able to be employed with lipoic acid, mention may be made of vitamin E, glutathione, vitamin A and vitamin C.

The combination of lipoic acid and taurine and the other antioxidant agent(s) may be employed together in the same composition or in separate compositions. Advantageously, the lipoic acid:antioxidant(s) ratio applied in the same composition or in separate compositions ranges from 0.001 to 0.01.

According to a particular embodiment of the invention, the combination of lipoic acid and taurine is employed with another osmoprotectant and/or at least one anti-inflammatory agent and/or at least one antioxidant in the same composition, preferably in the proportions described above.

According to another embodiment of the invention, the composition also comprises a mucomimetic polymer, in particular hyaluronic acid and salts thereof.

The composition comprising the combination of lipoic acid and taurine according to the invention may further comprise agents with moisturizing, healing, anti-inflammatory, anti-aging, soothing, anti-irritation, restructuring or emollient action, alone or in mixtures in any proportion.

According to a particular embodiment of the invention, the composition also comprises hyaluronic acid or salts thereof, preferably in a proportion of 0.05 to 2 wt % relative to the total weight of the composition. The various forms of hyaluronic acid and salts thereof employed in pharmaceutical or cosmetic compositions are well-known to a person skilled in the art and may be employed in the compositions according to the invention. Mention may be made notably of sodium hyaluronate with an intrinsic viscosity of 1 to 2.5 m$^3$/kg.

According to a preferred embodiment of the invention, the composition containing the combination of lipoic acid and taurine according to the invention is a preservative-free composition.

The preservatives generally employed in topical compositions (cosmetic, pharmaceutical, ophthalmic, etc.) to prevent their contamination by germs, are well-known to a person skilled in the art, such as quaternary ammoniums, notably benzalkonium chloride, alkyl-dimethyl-benzylammonium, cetrimide, cetylpyridinium chloride, benzododecinium bromide, benzethonium chloride, cetalkonium chloride; mercury-based preservatives, such as phenylmercuric nitrate/acetate/borate, thiomersal; alcohol-based preservatives, such as chlorobutanol, benzyl alcohol, phenylethanol, phenylethyl alcohol; carboxylic acids, such as sorbic acid; phenols, in particular methyl/propyl paraben; amidines, for example chlorhexidine digluconate; and/or chelators such as EDTA; alone or in combination with at least one other preservative.

According to the invention, "preservative-free" means a composition substantially free of such preservatives in order to satisfy a "preservative-free" indication. Its preservative content is 10 ppm or less, more particularly 1 ppm or less, preferably equal to 0 ppm, with no preservative comprised in its composition.

In the absence of preservatives, the composition must undergo special treatment during its preparation and packaging so as to avoid and prevent contamination by pathogens. These treatments and procedures are well-known to a person skilled in the art. In this sense, a preservative-free composition according to the invention is distinguished from a simple composition comprising the same ingredients obtained without specifying special precautions or describing the steps of the method for obtaining this sterility characteristic of the compositions according to the invention, in particular ophthalmic compositions.

According to a first particular embodiment of the invention, the combination of lipoic acid and taurine is used in the form of a topical composition suitable for application to the skin, particularly selected from creams, salves, gels, ointments, solutions and lotions.

The combination of lipoic acid and taurine is advantageously used as osmoprotectant for preventing and treating a skin condition in which dry skin appears, notably atopic dermatitis, ichthyosis, eczema or psoriasis.

A person skilled in the art knows how to prepare topical pharmaceutical or cosmetic compositions in these various forms, whether they are water-in-oil or oil-in-water emulsions, solutions, suspensions or gels. The components of these compositions and the proportions in which they are employed are well-known to a person skilled in the art and are described notably in the French Pharmacopeia.

Advantageously, the topical compositions according to the invention are preservative-free.

In these topical compositions for application to the skin, the proportion of lipoic acid is advantageously from 0.0001 to 0.1 wt % relative to the total weight of the composition, preferably from 0.001 to 0.05 wt %, in particular about 0.01 wt %.

The proportion of taurine is advantageously from 0.001 to 1.0 wt % relative to the total weight of the composition, preferably from 0.01 to 0.1 wt %, more preferably about 0.05 wt %.

The lipoic acid:taurine weight ratio in a cosmetic composition is preferably from 0.002 to 0.2, advantageously from 0.004 to 0.05, in particular from 0.01 to 0.05, more preferably about 0.02.

Advantageously, the dry matter content is between 0.001 and 0.05 wt %. Dry matter consists of all the components comprised in the composition of the formulation, excluding water.

According to another embodiment, the combination of lipoic acid and taurine is used in the form of an ophthalmic composition (solution, gel, emulsion, suspension) and the invention also relates to the combination of lipoic acid and taurine for use as osmoprotectant for preventing and treating eye disorders related to dry eye, which may be a sign of Meibomian gland dysfunction, hyperevaporative syndrome or lacrimal insufficiency, and for use in ocular edema, notably in corneal edema.

The combination of lipoic acid and taurine is advantageously used in the form of an ophthalmic composition suitable for application to the eye of a human or an animal subject, more particularly a human subject. Consequently, the ophthalmic composition must satisfy the specific technical characteristics of ophthalmic compositions, and more particularly those related to the selection of its components. These "ophthalmically acceptable" components must not, individually or combined in the composition, cause secondary reactions of the eye apart from the effect sought by the composition and the active agents thereof. The eye being an organ which is particularly sensitive to environmental stress, the composition must not cause parasitic irritations or allergic-type reactions to the detriment of the effect sought, more particularly in the case of ophthalmic compositions intended to treat an ophthalmic condition. The choice of the components of the composition is thus very important, which distinguishes the ophthalmic composition from a simple composition unsuited to ophthalmic use. A person skilled in the art is able to choose said components and to differentiate an ophthalmic composition from a simple composition intended for another use.

The ophthalmic composition preferably has a pH between 5 and 7.5. It thus generally comprises a buffer suitable for ophthalmic use, known to a person skilled in the art. Particular mention may be made of trisodium citrate dihydrate and citric acid monohydrate employed alone or in mixture.

The ophthalmic composition must also be sterile in order not to introduce pathogens able to develop and to lead to ophthalmic complications. Within the meaning of the present invention, "sterile" means the absence of microbes within the meaning of the European Pharmacopoeia, $8^{th}$ edition (2014). Preferably, the ophthalmic composition which comprises the combination of lipoic acid and taurine according to the invention is a preservative-free composition.

Ophthalmic compositions are generally in the form of liquids, solutions or emulsions, but also in the form of gels or ointments. The ophthalmic composition according to the invention is preferably a solution or a liquid emulsion for application by instillation of one or more drops in the eye. The viscosity of the liquid composition is nevertheless selected so as to allow it to remain on the eye, in particular on the cornea, for a period sufficient to allow it to act.

The ophthalmic composition according to the invention preferably has a viscosity of 5 to 100 centipoises. This viscosity is measured according to the recommendations of the European Pharmacopoeia 2.2.10, with a rotating viscometer, at 25° C., and 100 $s^{-1}$. Other measuring devices and methods suitable for measuring the viscosity of solutions are known to a person skilled in the art and provide similar results.

The viscosity of the ophthalmic composition according to the invention depends on its form (solution or emulsion) and is adjusted by adding "ophthalmically acceptable" viscosity agents. A person skilled in the art is well familiar with the viscosity agents able to be employed for the preparation of ophthalmic compositions and the amounts to be used to obtain the viscosity sought. Particular mention may be made of hydroxypropylmethylcellulose, hydroxyethylcellulose, carboxymethylcellulose, carbomers, agar gels, polyvinylpyrrolidone and polyvinyl alcohol.

Preferably, the ophthalmic composition according to the invention comprises hydroxypropylmethylcellulose or carboxymethylcellulose, preferably in a proportion of 0.05 to 0.5 wt % hydroxypropylmethylcellulose or carboxymethylcellulose, advantageously from 0.1 to 0.4 wt %, more advantageously from 0.2 to 0.3 wt %, particularly about 0.25 wt %.

Unless otherwise specified, the percentages are expressed by weight relative to the total weight of the composition.

The ophthalmic composition comprising lipoic acid according to the invention advantageously comprises from 0.0001 to 0.1 wt % lipoic acid relative to the total weight of the composition, and preferably at least 0.001 wt %, more preferably about 0.001 wt %.

The proportion of taurine is advantageously from 0.01 to 1.0 wt % relative to the total weight of the composition, preferably from 0.01 to 0.05 wt %.

The lipoic acid:taurine weight ratio in an ophthalmic composition is preferably from 0.002 to 0.2, advantageously from 0.004 to 0.05.

Among the preferred ophthalmic compositions according to the invention mention may be made of the compositions below.

According to a preferred embodiment of the invention, the ophthalmic composition comprising lipoic acid according to the invention is an oil-in-water emulsion.

The invention also relates to a method for preventing and treating diseases of the skin and of the mucous membranes associated with osmotic imbalance, in which a suitable amount a combination of lipoic acid and taurine as osmoprotectant is applied to the skin or to the mucous membranes, including to the eye, of a patient in need thereof.

The combination of lipoic acid and taurine will advantageously be applied to the skin, to the mucous membranes or to the eye by means of a composition as defined above and in the examples.

The suitable amount of the combination of lipoic acid and taurine applied will depend on the condition treated, but also on its severity. The patient's age or corpulence may also influence the practitioner in the choice of the amount to be applied.

Application of the suitable amount may be carried out in one application, or in several daily applications, for the time necessary to obtain the effect sought, i.e., the prevention or treatment of diseases of the skin and of the mucous membranes, in particular of the eye, associated with osmotic imbalance.

In the case of a liquid ophthalmic composition for instillation, the suitable amount will be given as the number of drops to be instilled.

EXAMPLES

Figure 1:
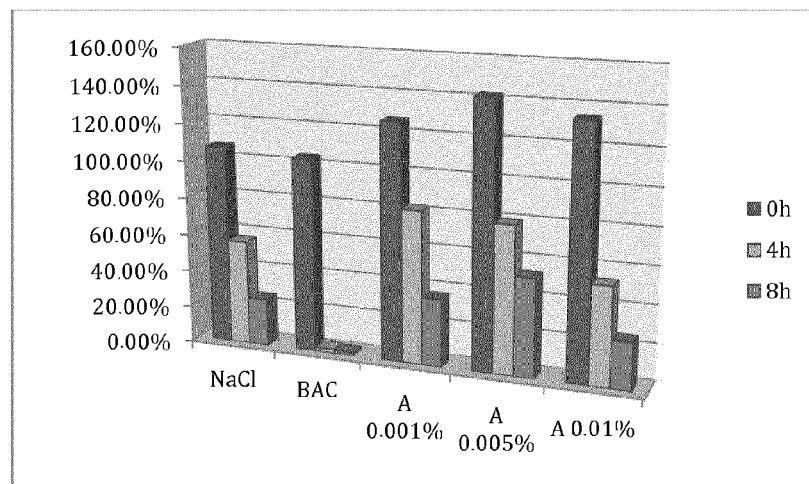
FIGS. 1 to 4 represent cell viability results after osmotic stress for various concentrations of lipoic acid, alone or combined with glycerin and/or taurine.

The compositions given in the following examples are prepared according to the usual methods of the technical field. Specific sanitary precautions are taken for the preparation and packaging of preservative-free compositions so as to avoid contamination.

Example 1: Dermatological Composition

| Components | Amount |
|---|---|
| Caprylic/capric triglyceride | 20.00% |
| Tribehenin PEG-20 esters | 3.00% |
| Niacinamide | 3.00% |
| Taurine | 0.50% |
| Glycerin | 0.50% |
| Allantoin | 0.20% |
| Sodium lipoate | 0.01% |
| Ceramide 3 | 0.10% |
| Sodium hyaluronate | 0.20% |
| Sodium lipoate | 0.01% |
| Sodium hydroxide (10% solution) | 1.50% |
| Reverse-osmosis water | q.s. 100% |

Example 2: Dermatological Composition

| Components | Amount |
|---|---|
| Cocamidopropyl betaine | 10.00% |
| Decyl glucoside | 5.00% |
| Glycerin | 5.00% |
| Niacinamide | 2.00% |
| Trisodium citrate dihydrate | 1.45% |
| Xanthan gum | 0.75% |
| Taurine | 0.50% |
| Allantoin | 0.20% |
| Sodium hyaluronate | 0.10% |
| Citric acid | 0.025% |
| Lipoic acid | 0.005% |
| Water | q.s. 100% |

Example 3: Dermatological Composition

| Components | Amount |
|---|---|
| Caprylic/capric triglyceride | 25.00% |
| Niacinamide | 4.00% |
| Tribehenin PEG-20 esters | 3.50% |
| Glycerin | 3.00% |
| Trisodium citrate | 1.45% |
| Xanthan gum | 0.80% |
| Taurine | 0.50% |
| Allantoin | 0.50% |
| Sodium hyaluronate | 0.10% |
| Ceramide NP | 0.10% |
| Citric acid | 0.05% |
| Lipoic acid | 0.05% |
| Water | q.s. 100% |

Example 4: Dermatological Composition

| Components | Amount |
|---|---|
| Caprylic/capric triglyceride | 20.00% |
| Tribehenin PEG-20 esters | 3.00% |
| Glycerin | 3.00% |
| Trisodium citrate | 1.45% |
| Xanthan gum | 0.80% |
| Sodium hyaluronate | 0.50% |
| Taurine | 0.50% |
| Allantoin | 0.20% |
| *Helianthus annuus* (sunflower oil), | 0.10% |

-continued

| Components | Amount |
|---|---|
| Retinyl palmitate | |
| Citric acid | 0.05% |
| Lipoic acid | 0.01% |
| Water | q.s. 100% |

Example 5: Ophthalmic Composition

| Components | Amount |
|---|---|
| Sodium hyaluronate | 0.20% |
| Taurine | 0.5% |
| Sodium lipoate | 0.001% |
| Caprylic/capric triglyceride | 0.05% |
| Soy lecithin | 0.15% |
| Sodium carboxymethylcellulose | 0.15% |
| Trisodium citrate dihydrate | 0.05% |
| Citric acid | 0.02% |
| NaOH (1N) | q.s. pH 6.7 |
| Sodium chloride | q.s. 150 mOsmol/L |
| Water for injection | q.s. 100% |

Example 6: Ophthalmic Composition

| Components | Amount |
|---|---|
| Sodium chloride | 5.00% |
| Sodium hyaluronate | 0.18% |
| Taurine | 0.1% |
| Lipoic acid | 0.001% |
| Sodium carboxymethylcellulose | 0.3% |
| Disodium citrate dihydrate | 1.5% |
| Citric acid monohydrate | q.s. pH 7 |
| Purified water | q.s. 100% |

Example 4—Osmoprotective Activity of Lipoic Acid and Taurine Alone or in Mixtures A study was carried out to determine the osmoprotective capacity of sodium lipoate (A) during hyperosmolar stress on human conjunctival (WKD) and corneal (HCE) cells.

In a second phase, tests were carried out to compare the effect of lipoic acid, glycerin (B), and taurine (C), individually and when the molecules were combined, on HCE cells under hyperosmolar stress conditions.

The osmoprotective activity of A, then A with B and C, was evaluated by measuring cell viability in particular. To that end, cells were preincubated for 17 h with the test substance(s). Next, the medium was removed and the cells were subjected to hyperosmolar stress by addition of sodium chloride (100 mM NaCl) to the culture medium (M199 for the WKD cells and KSFM for the HCE cells). Cell-growth control cells were contacted with isotonic medium. Cell viability was analyzed pre-osmotic stress (0 h) in order to measure the effect of the molecules remaining in contact with the cells during the 17 h of incubation, then at 4 h, 8 h and 24 h post-induction of osmotic stress. The cell viability measurement was carried out via an XTT assay.

Various concentrations of A were tested for the "molecule alone" tests: 0.0005%, 0.001%, 0.005%, 0.01% and 0.05% w/v. For the molecule mixture tests, the following concentrations were tested: for A: 0.001%, 0.005%, and 0.01% w/v; for B: 0.25% w/v; and for C: 0.5% and 1% w/v.

To ensure the validity and the significance of the data, the results obtained were analyzed statistically. The results presented below result from the mean of 3 independent repetitions, carried out on different days.

Cell Viability Measurements for Various Concentrations of Lipoic Acid (Sodium Lipoate) with WKD Cells

| | 0 h | 4 h | 8 h | 24 h |
|---|---|---|---|---|
| At 0.0005% | 99.90% | 62.70% | 38.50% | 18.80% |
| At 0.001% | 98.50% | 69.60% | 42.40% | 18.50% |
| At 0.005% | 102.80% | 109.40% | 76.10% | 12.60% |
| At 0.01% | 98.10% | 119.90% | 82.90% | 8.90% |
| At 0.05% | 56.30% | 46.00% | 27.80% | 2.70% |
| NaCl | 98.80% | 50.70% | 33.50% | 25.80% |
| HIDC | 92.30% | 68.80% | 50.40% | 56.40% |

Cell viability measurements for various concentrations of lipoic acid (sodium lipoate) with HCE cells are shown in FIG. 1.

Lipoic acid has high osmoprotective activity against osmotic stress at 0.005% and 0.001% (w/v) at 4 h and 8 h post-stress.

Figure 2:
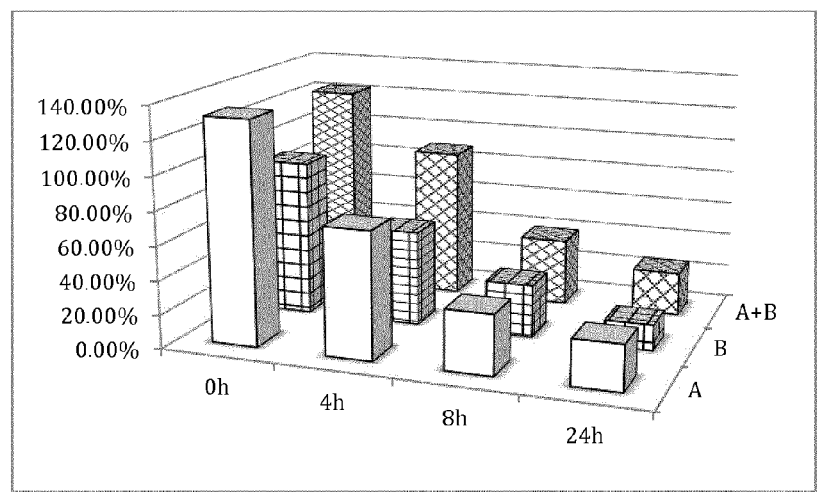
Figure 3:
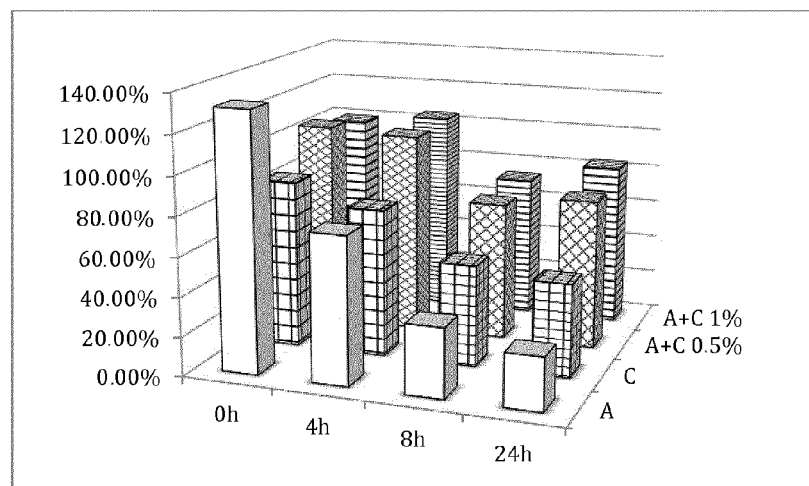
Figure 4:
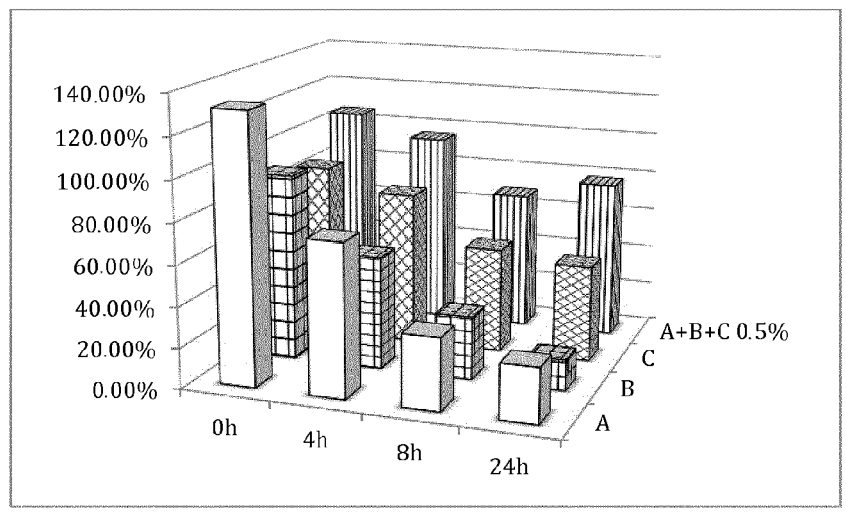

FIGS. 2 to 4 represent the viability results obtained with various mixtures of A with B, C and B+C.

An enhanced osmoprotective effect of lipoic acid is observed when it is combined with glycerin (B) and with taurine (C), or with both. This enhancement is expressed as higher cell viability than that observed with lipoic acid alone, with glycerin alone or with taurine alone. It is particularly marked for the combination lipoic acid+taurine (FIG. 3), which increases said osmoprotective action over time, up to 24 h post-stress.

Example 5—Osmoprotective Activity of Mixtures of Lipoic Acid and Taurine

The protocol of Example 4 is repeated with 11 mixtures (M1 to M11) of sodium lipoate (A) and taurine (B). The cell viability results obtained confirm the increase in osmoprotective action over time observed for the mixtures of Example 4.

Cell Viability Measurements for Various Concentrations of Lipoic Acid (Sodium Lipoate—A) and Taurine (B) with WKD Cells

| | A % | C % | A/C | t = 0 h | t = 4 h | t = 8 h | t = 24 h |
|---|---|---|---|---|---|---|---|
| M1 | 0.0001 | 0.10 | 0.001 | 81% | 63% | 50% | 33% |
| M2 | 0.0002 | 0.10 | 0.002 | 84% | 66% | 51% | 32% |
| M3 | 0.0050 | 1.00 | 0.005 | 84% | 70% | 67% | 54% |
| M4 | 0.0050 | 0.50 | 0.010 | 93% | 72% | 66% | 52% |
| M5 | 0.0050 | 0.25 | 0.020 | 96% | 78% | 65% | 46% |
| M6 | 0.0100 | 0.50 | 0.020 | 96% | 73% | 69% | 51% |
| M7 | 0.0200 | 1.00 | 0.020 | 82% | 63% | 58% | 50% |
| M8 | 0.0200 | 1.00 | 0.020 | 90% | 64% | 57% | 40% |
| M9 | 0.0050 | 0.10 | 0.050 | 92% | 74% | 58% | 36% |
| M10 | 0.0500 | 0.25 | 0.200 | 61% | 49% | 40% | 21% |
| M11 | 0.0500 | 0.10 | 0.500 | 73% | 52% | 27% | 19% |
| Control (NaCl) | | | | 94% | 68% | 46% | 22% |

The improved osmoprotective effect appears even more marked for the preferred lipoic acid:taurine weight ratio, which ranges from about 0.004 to about 0.05 (mixtures M3 to M9).

REFERENCES

U.S. Pat. No. 5,817,630
U.S. Pat. No. 6,162,393
US 2004/265345
US 2005/192229
US 2006/188492
WO 01/93824
WO 02098345
DE10229995
BR PI0 800 818
CN 103 860 625
JP 2013 241398
Masami Kojima et al., Japanese Journal of Ophthalmology, January 2007, Volume 51, Issue 1, pp 10-13

The invention claimed is:

1. A pharmaceutical or cosmetic composition for topical application comprising a combination of lipoic acid and taurine and a pharmaceutically or cosmetically acceptable carrier, wherein said composition comprises from 0.001 to 0.1 wt % lipoic acid and from 0.2 to 1.0 wt % taurine relative to the total weight of the composition and wherein the lipoic acid:taurine weight ratio ranges from 0.004 to 0.05.

2. The composition of claim 1, wherein said composition is suitable for application to the skin, and wherein said composition is selected from the group consisting of creams, salves, gels, lotions, solutions, emulsions and ointments.

3. The composition of claim 2, wherein said composition comprises from 0.005 to 0.05 wt % lipoic acid relative to the total weight of the composition.

4. The composition of claim 1, that is an ophthalmic composition suitable for application to the eye.

5. A method for treatment of a skin condition in which dry skin appears in a patient in need thereof, comprising applying the composition according to claim 1 to skin of said patient.

6. The method of claim 5, wherein said composition is suitable for application to the skin, and further wherein said compositions is selected from the group consisting of creams, salves, gels, lotions, solutions, emulsions and ointments.

7. The method of claim 5, wherein the skin condition is selected from the group consisting of atopic dermatitis, ichthyosis, eczema and psoriasis.

8. A method for treatment of an eye condition related to dry eye in a patient in need thereof, comprising applying the composition according to claim 1 to an eye of said patient.

9. The method of claim 8, wherein the composition comprises from 0.5 wt % taurine relative to the total weight of the composition.

10. The method of claim 8, wherein the eye condition related to dry eye is a sign of Meibomian gland dysfunction, hyperevaporative syndrome or lacrimal insufficiency.

11. A method for the treatment of ocular edema, optionally in corneal edema, in a patient in need thereof, comprising applying the composition according to claim 1 to the eye of said patient.

12. The composition according to claim 1, wherein the composition is substantially free of preservatives.

13. The composition of claim 1, wherein the lipoic acid:taurine weight ratio ranges from 0.01 to 0.05.

14. The composition of claim 1, wherein the lipoic acid:taurine weight ratio is 0.02.

15. The composition of claim 2, comprising 0.01 wt % lipoic acid relative to the total weight of the composition.

16. The composition of claim 2, comprising 0.5 wt % taurine relative to the total weight of the composition.

17. The composition of claim 1, wherein dry matter content is between 0.001 and 0.05 wt. %.

18. The composition of claim 1, wherein said composition is an osmoprotectant used to prevent and treat ailments of the skin and mucus membranes associated with osmotic imbalance.

19. A pharmaceutical or cosmetic composition for topical application comprising a combination of lipoic acid and taurine and a pharmaceutically or cosmetically acceptable carrier, wherein said composition comprises from 0.005 to 0.02 wt % lipoic acid and 0.5 wt % taurine relative to the total weight of the composition, and wherein the lipoic acid:taurine weight ratio is 0.01 to 0.04.

* * * * *